(12) United States Patent
Creek et al.

(10) Patent No.: US 7,573,571 B2
(45) Date of Patent: Aug. 11, 2009

(54) AIRBORNE PARTICULATE DISCRIMINATOR

(75) Inventors: Kathryn Louise Creek, San Diego, CA (US); Alonso Castro, Santa Fe, NM (US); Perry Clayton Gray, Los Alamos, NM (US)

(73) Assignee: Los Alamos National Security LLC, Los Alamos, NM (US)

( * ) Notice: Subject to any disclaimer, the term of this patent is extended or adjusted under 35 U.S.C. 154(b) by 0 days.

(21) Appl. No.: 11/871,678

(22) Filed: Oct. 12, 2007

(65) Prior Publication Data

US 2009/0095053 A1 Apr. 16, 2009

(51) Int. Cl.
*G01J 3/30* (2006.01)
(52) U.S. Cl. .................................. 356/317; 250/458.1
(58) Field of Classification Search ... 250/458.1–461.2; 422/82.07–82.08; 73/28.01; 436/172
See application file for complete search history.

(56) References Cited

U.S. PATENT DOCUMENTS 6,814,934 B1 * 11/2004 Higuchi ................ 422/82.08
7,289,203 B2 * 10/2007 Frankel ..................... 356/301
7,319,039 B2 * 1/2008 Sullivan .................... 436/172

* cited by examiner

*Primary Examiner*—Kara E Geisel
*Assistant Examiner*—Abdullahi Nur
(74) *Attorney, Agent, or Firm*—John P. O'Banion (57) ABSTRACT

A method and apparatus for rapid and accurate detection and discrimination of biological, radiological, and chemical particles in air. A suspect aerosol of the target particulates is treated with a taggant aerosol of ultrafine particulates. Coagulation of the taggant and target particles causes a change in fluorescent properties of the cloud, providing an indication of the presence of the target.

6 Claims, 9 Drawing Sheets

| Test Number | (Bound dye)/ 3 STD Room Air 1 minute | (Bound dye)/ 3 STD Room Air 2 minutes | (Bound dye)/ 3 STD Room Air 10 minutes | Detection outcome |
|---|---|---|---|---|
| 1 | 14 | 32 | 320 | Positive |
| 2 | 21 | 43 | 292 | Positive |
| 3 | 14 | 33 | 242 | Positive |
| 4 | 11 | 27 | 204 | Positive |
| 5 | 24 | 58 | 486 | Positive |
| 6 | 18 | 44 | 369 | Positive |
| 7 | 8 | 27 | 309 | Positive |
| 8 | 14 | 34 | 348 | Positive |
| 9 | 17 | 34 | 268 | Positive |
| 10 | 24 | 50 | 198 | Positive |
| 11 | 32 | 68 | 395 | Positive |
| 12 | 18 | 37 | 209 | Positive |
| 13 | 24 | 56 | 241 | Positive |
| 14 | 17 | 37 | 316 | Positive |
| 15 | 20 | 45 | 441 | Positive |

FIG. 11A

| Test Number | (Bg + Bound dye)/ 3 STD Room Air 1 minute | (Bg + Bound dye)/ 3 STD Room Air 2 minutes | (Bg + Bound dye)/ 3 STD Room Air 10 minutes | Detection outcome |
|---|---|---|---|---|
| 1 | 78 | 92 | 337 | Positive |
| 2 | 96 | 113 | 348 | Positive |
| 3 | 71 | 86 | 285 | Positive |
| 4 | 64 | 77 | 243 | Positive |
| 5 | 117 | 143 | 555 | Positive |
| 6 | 96 | 116 | 429 | Positive |
| 7 | 82 | 95 | 360 | Positive |
| 8 | 91 | 106 | 405 | Positive |
| 9 | 88 | 100 | 322 | Positive |
| 10 | 137 | 156 | 288 | Positive |
| 11 | 155 | 184 | 490 | Positive |
| 12 | 78 | 92 | 254 | Positive |
| 13 | 132 | 158 | 324 | Positive |
| 14 | 115 | 130 | 390 | Positive |
| 15 | 115 | 134 | 509 | Positive |

FIG. 11B

AIRBORNE PARTICULATE DISCRIMINATOR

STATEMENT REGARDING FEDERALLY SPONSORED RESEARCH OR DEVELOPMENT

This invention was made with Government support under Contract No. DE-AC52-06NA25396, awarded by the Department of Energy. The Government has certain rights in this invention.

CROSS-REFERENCE TO RELATED APPLICATIONS

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to particle detection, and more particularly to detection of airborne particles, including biological, chemical and radiological agents.

2. Description of Related Art

There is a need to detect airborne particulates, particularly respirable size particles, for various health, environmental, safety and security reasons. Airborne particulate contaminants, both man-made and naturally occurring, are all around us. Some can be extremely hazardous. Airborne biological, radiological or chemical particulates pose a terrorist threat. The Threat Agent Cloud Tactical Intercept And Countermeasure (TACTIC) program is directed to developing detection technologies to identify these potential threats. The objective is to detect an agent in about one minute, with a probability of detection of at least 0.9 and a probability of false alarm of less than 0.01.

One approach is to sample air and to collect particles in a media, and then submit the media to a laboratory for analysis. While this approach may be accurate, it is cumbersome and slow. Another approach is to use uv/vis excitation with scattered or fluorescent light detection, which is real-time, but does not effectively discriminate or identify the particulate type.

Accordingly it is desirable to provide an improved method and apparatus for detecting and discriminating airborne particulates. The method should be real-time and detect the particulates while airborne.

BRIEF SUMMARY OF THE INVENTION

The invention is method and apparatus for rapid and accurate detection and discrimination of biological, radiological, and chemical particles in air. A suspect aerosol of the target particulates is treated with a taggant aerosol of ultrafine taggant particulates. Coagulation of the taggant and target particles causes a change in luminescent properties of the cloud, providing an indication of the presence of the target.

An aspect of the invention is a method for detecting airborne target particulates, by injecting an aerosol of ultrafine taggant particulates into a region possibly containing the airborne target particulates so that the taggant particulates will bind with the target particulates if they are present; directing a light beam at the region into which the taggant aerosol was injected to excite taggant bound to target particulates; and detecting luminescence signals from the region, the luminescence signals being characteristic of the taggant binding to target particulates.

Another aspect of the invention is a method for detecting airborne biological particulates, by injecting an aerosol of ultrafine taggant particulates into a region possibly containing the airborne biological particulates so that the taggant particulates will bind or coagulate with the biological particulates if they are present, the taggant being specific to nucleic acids and exhibiting a large enhancement of fluorescence upon binding to the biological particulates; directing a light beam at the region into which the taggant aerosol was injected to excite taggant bound to target particulates; and detecting fluorescence signals from the region, the fluorescence signals being characteristic of the taggant binding to biological particulates.

A further aspect of the invention is an apparatus for detecting airborne target particulates, including a taggant aerosol source for injecting an aerosol of ultrafine taggant particulates into a region possibly containing the airborne target particulates so that the taggant particulates will bind or coagulate with the target particulates if they are present; a light source positioned to direct a light beam at the region into which the taggant aerosol was injected to excite taggant bound to target particles; and a detector positioned to receive luminescence signals from the region, the luminescence signals being characteristic of the taggant binding to target particulates.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the method, apparatus and data generally shown in FIG. 1 through FIG. 11B. It will be appreciated that the apparatus may vary as to configuration and as to details of the parts, and the method may vary as to its particular implementation, without departing from the basic concepts as disclosed herein.

The invention is directed towards the real-time, in air detection and discrimination of airborne particulates. The invention uses taggants in the form of ultrafine particulates to bind or coagulate with the airborne target particulates. The taggants are selected to be specific to a class of target particulates, e.g. biological particulates. The taggant may also be selected to be specific to a particular target particulate in cases of monitoring for the presence or absence of a single contaminant.

The taggant particles or droplets are ultrafine in size, preferably about half a micron or less. The ultrafine taggant has a large number of particulates per unit volume so that there is a high probability of contact and attachment to the target particulates. The target particulates are typically respirable particles, 1 to 10 microns in size. The use of submicron size ultrafine taggant particulates (aerosolized droplets) makes "dye-on-the-fly" tagging of respirable particulates possible.

The taggant is also chosen for the property of exhibiting a large enhancement of luminescence upon binding to the target particulates. The detection and discrimination scheme is based on this change in luminescence when the taggant binds to the target. Luminescence includes but is not limited to fluorescence, Raman scattering, and phosphorescence. The taggants are generally reporters that produce some type of observable signal when bound to the target particles, and are typically dyes, but also include but are not limited to quantum dots and scintillators.

Figure 1:
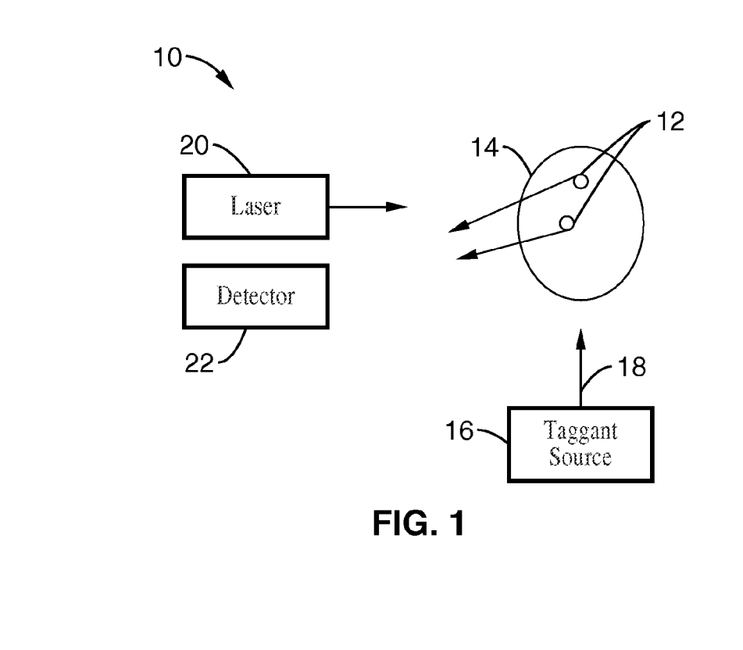
FIG. 1 is a simple block diagram of an airborne particulate discriminator apparatus of the invention

FIG. 1 illustrates an apparatus 10 for detecting airborne particulates 12 according to the invention. To detect target airborne particulates 12 in a region 14, a taggant source 16 delivers an aerosolized spray 18 of ultrafine taggant particulates (or droplets). A light source 20, e.g. laser, directs a light beam onto the region 14 to excite the bound taggant, and a detector 22 detects luminescent, e.g. fluorescent, signals from the tagged particulates 12. If the target particulate is present, then the light will excite a luminescent signal that will be detected. If the target particulate is not present, then the light will not excite a luminescent signal and no (or minimal) signal will be detected. The taggant source 16 may be mobile so that it can get close to the region 14, e.g. it could be on a truck or an airplane; light source 20 and detector 22 may be much farther away, e.g. 10 km, and may also be mobile.

Various light sources can be used as the excitation source. The source may be a solid state or other laser; or a flash lamp, or an assembly of a flash lamp and optical filter to select an excitation wavelength, or a flash lamp with dispersive optical elements (e.g. gratings, monochromator, spectrometer) to limit the wavelength of excitation. A broad band excitation source (e.g. flash lamp) may be employed with long excitation lifetime taggants for time resolved fluorescence detection. A short pulse laser may be used for time resolved detection. Any of the above sources may be used with optically dispersive elements (e.g. optical gratings, monochromater, spectrometer) to limit excitation wavelength.

Various detectors can also be used, including a photomultiplier tube with optical filter to limit the detection wavelength; a solid state diode with optical filter; a solid state diode for time resolved detection; and a CCD detector with filter. Any of the above detectors can be used with an optically dispersive element (e.g. optical gratings, monochromater, spectrometer) to limit detection wavelength.

A particular application of the invention is to detect biological particulates, which include viruses, bacteria, pollen/fungi, and spores. All biological materials are characterized by having nucleic acids or DNA. Intercalator dyes are particularly suitable for detecting biological materials since they are non-fluorescent in free solution but exhibit very large fluorescence quantum yield when bound to DNA. Examples of intercalator dyes are picogreen, TOTO, YOYO, and ethidium bromide.

Figure 2:
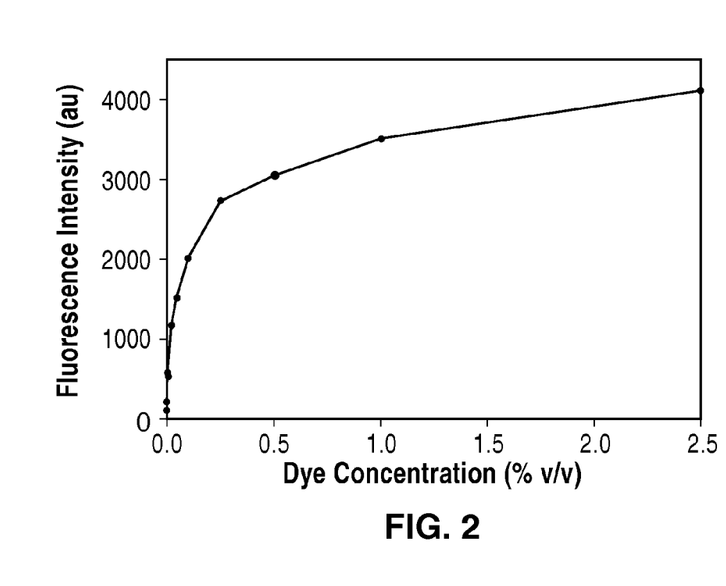
FIG. 2 is a graph of fluorescence intensity vs. taggant concentration for *Bacillus globigii* (Bg) spores tagged with an intercalator dye.
Figure 3:
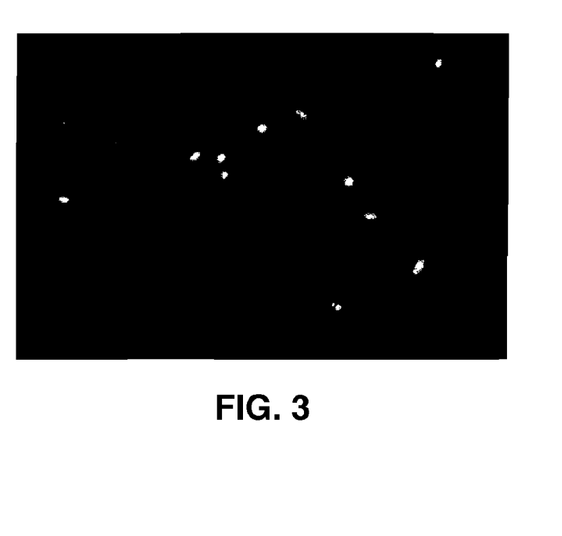
FIG. 3 is a micrograph of Bg spores treated with taggant solution.
Figure 4:
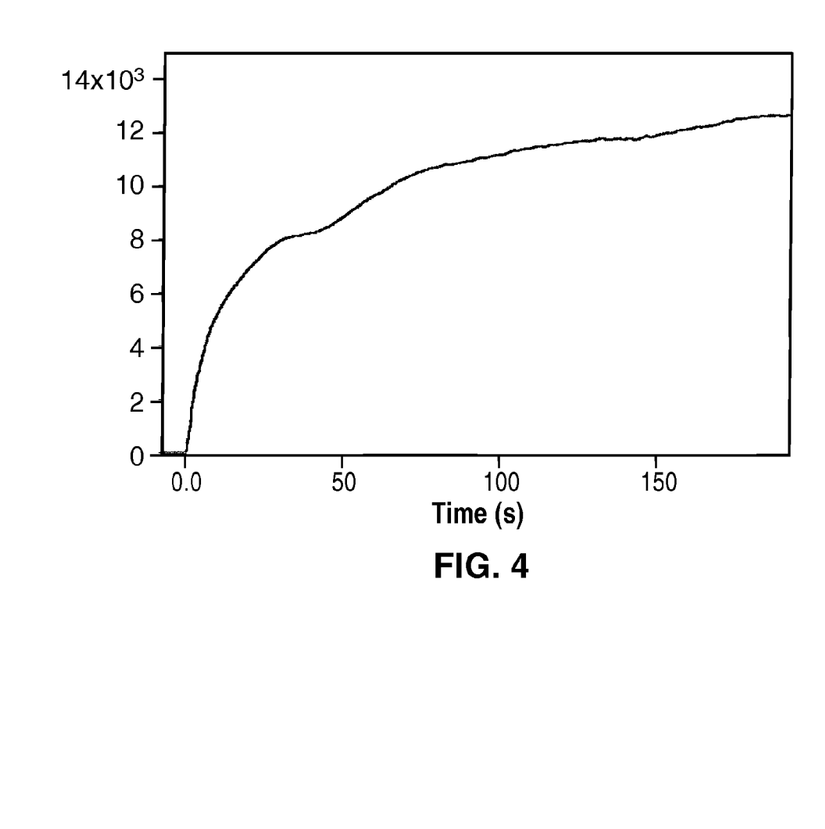
FIG. 4 is a graph showing the time evolution of fluorecence enhancement.

FIG. 2 is a graph of fluorescence intensity vs. taggant concentration for *Bacillus globigii* (Bg) spores tagged with an intercalator dye. The optimum taggant concentration appears to be around 2% v/v for a $10^6$ spores/mL Bg suspension. FIG. 3 is a micrograph of Bg spores treated with taggant solution. FIG. 4 shows that the large fluorescence enhancements are observed in just a few seconds.

While the invention is intended to be used in situ, it has been tested in a closed test facility having an aerosol chamber with a volume of about 0.68 m$^2$, with Bg as the biological target and picogreen as the taggant. Once the Bg is disseminated as an aerosol, the picogreen DNA dye is also aerosolized into the chamber with the Bg. Picogreen exhibits a large enhancement of fluorescence upon binding to Bg spores (fluorecence enhancements of 2000 times have been observed in solution). A 488 nm argon laser is directed into the chamber to excite the tagged Bg aerosol. The laser beam is reflected several times between arrays of parallel mirrors. Fluorescence images in the 525-565 nm band are acquired at right angles with a cooled CCD camera. Detection of fluorescence enhancements signifies the presence of Bg.

Figure 5:
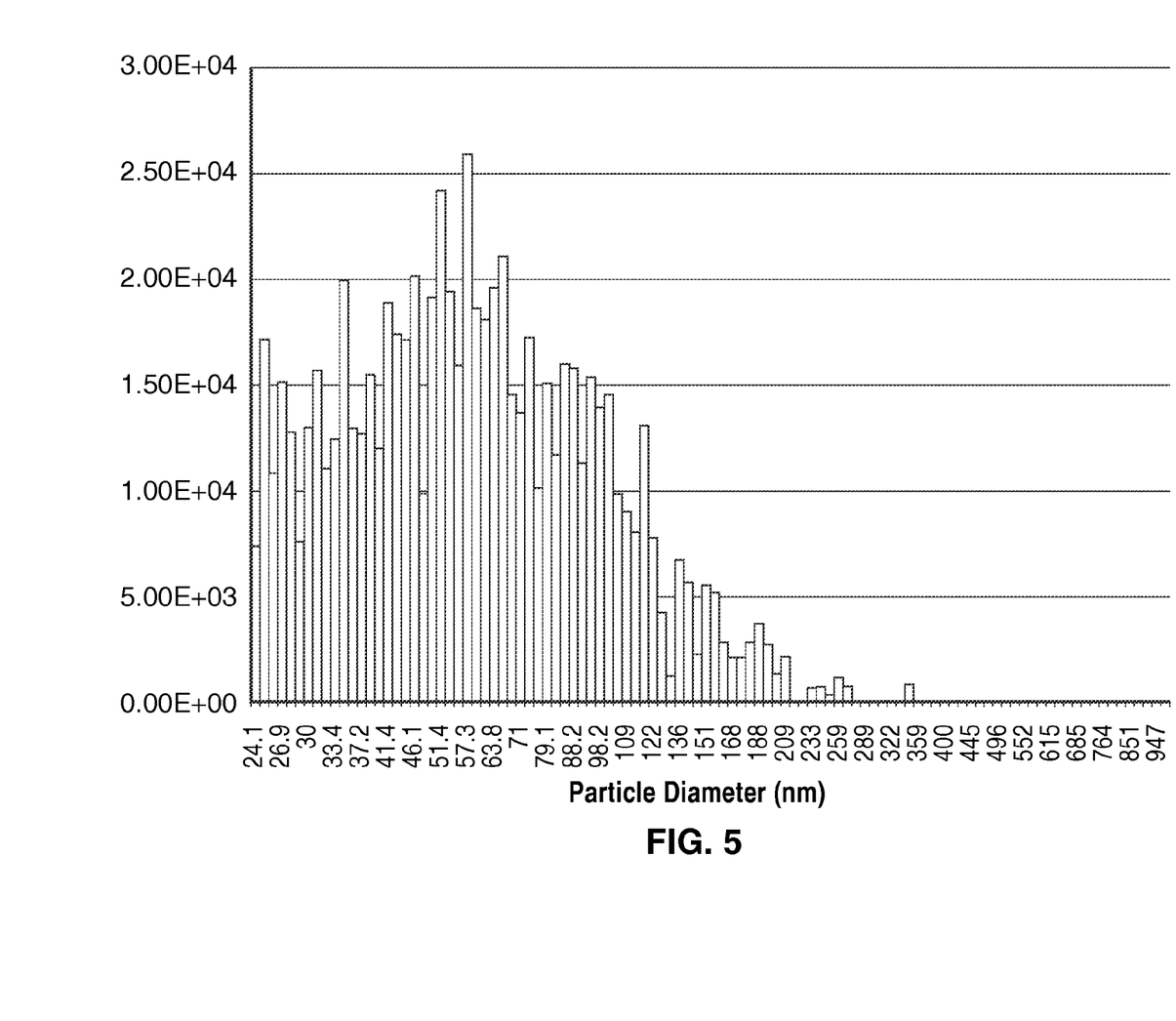
FIG. 5 is a particle size distribution histogram of aerosolized picogreen dye.

The test procedure had two main parts: a room air tagging experiment to evaluate the false positive rate, and a Bg spore in room air tagging experiment to evaluate the sensitivity of the technique. In the first part, the free dye in air signal is obtained by injecting a dye solution into the chamber. Four nebulizers were used to introduce a picogreen dye and water solution into the test chamber. Stock picogreen dye is a 0.0003 molar solution in DMSO. 200 µL of stock picogreen dye solution was diluted with 10 mL of water to produce a concentration of $3.6 \times 10^{15}$ picogreen molecules per mL of injector solution. Approximate injector flow rates were 0.2 mL/min per nebulizer, which yields an approximate concentration of $4 \times 10^9$ picogreen molecules/cm$^3$ at the 1 minute mark. A typical particle size distribution histogram of the aerosolized picogreen dye is shown in FIG. 5. The sizes mostly are in the about 25 to about 210 nm range.

Figure 6:
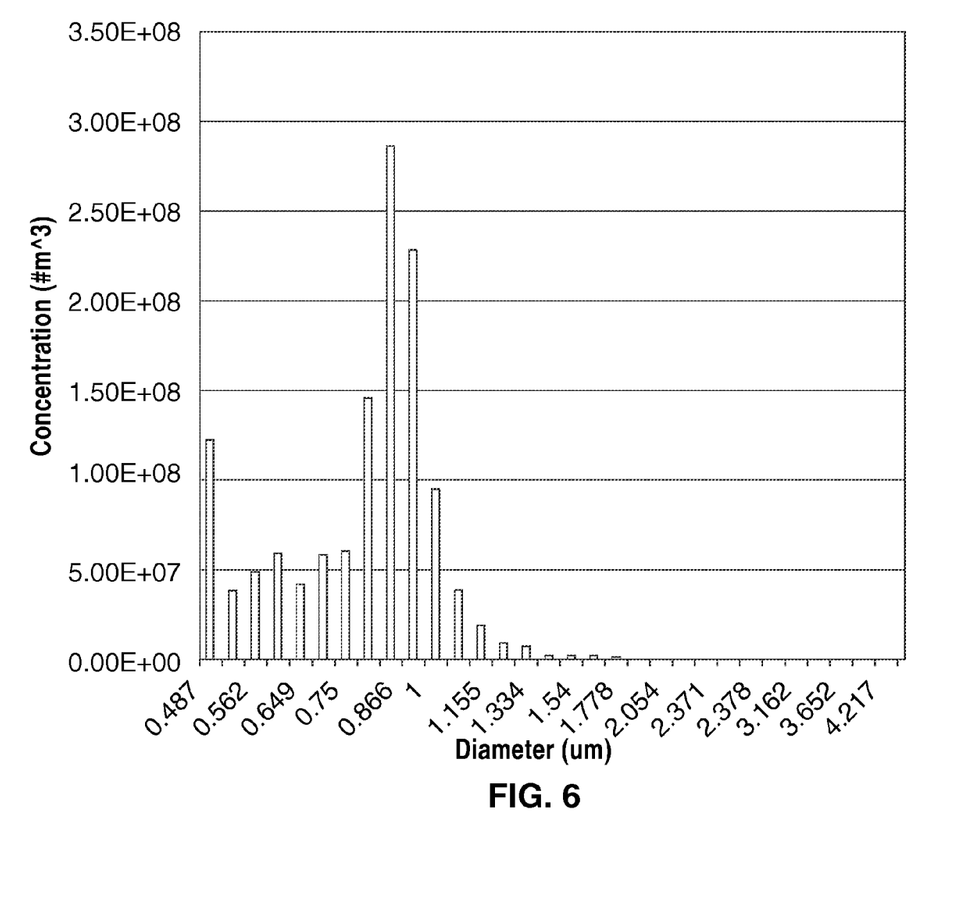
FIG. 6 is a particle size distribution histogram of aerosolized Bg spores.
Figure 7:
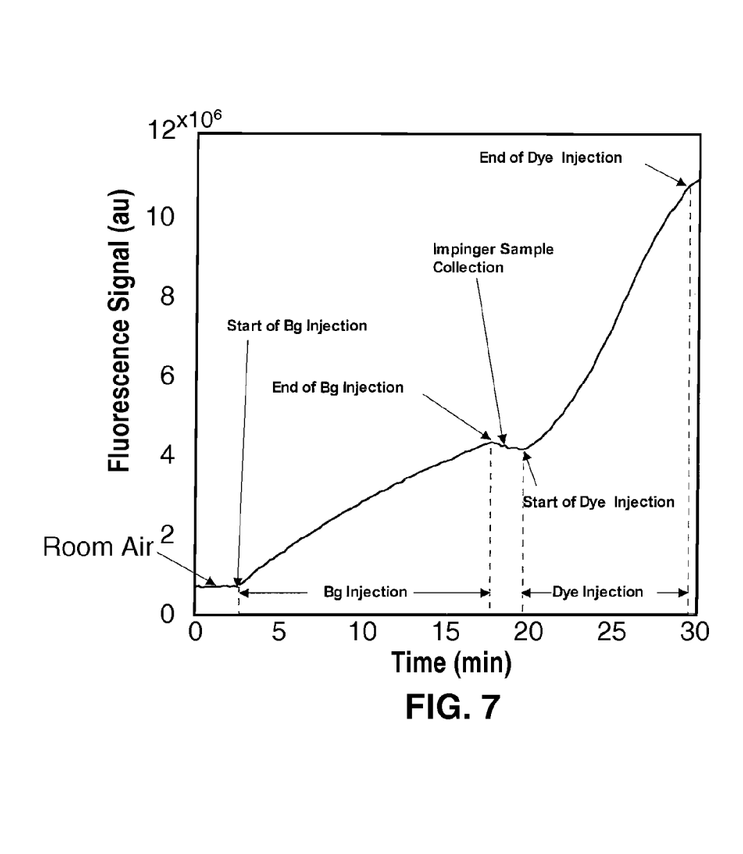
FIG. 7 is graph of the temporal evolution of fluorescence signals from the test chamber.
Figure 8:
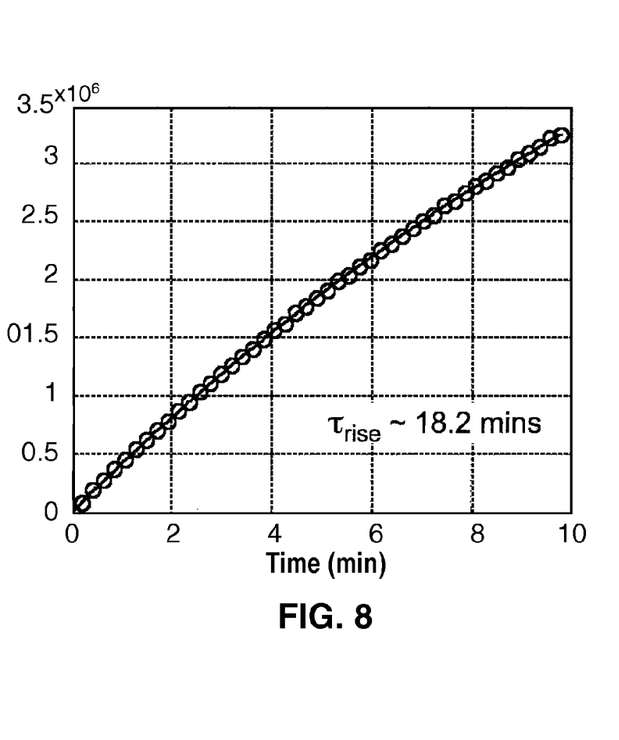
FIG. 8 is a graph of the rise in injected Bg concentration as a function of time.
Figure 9:
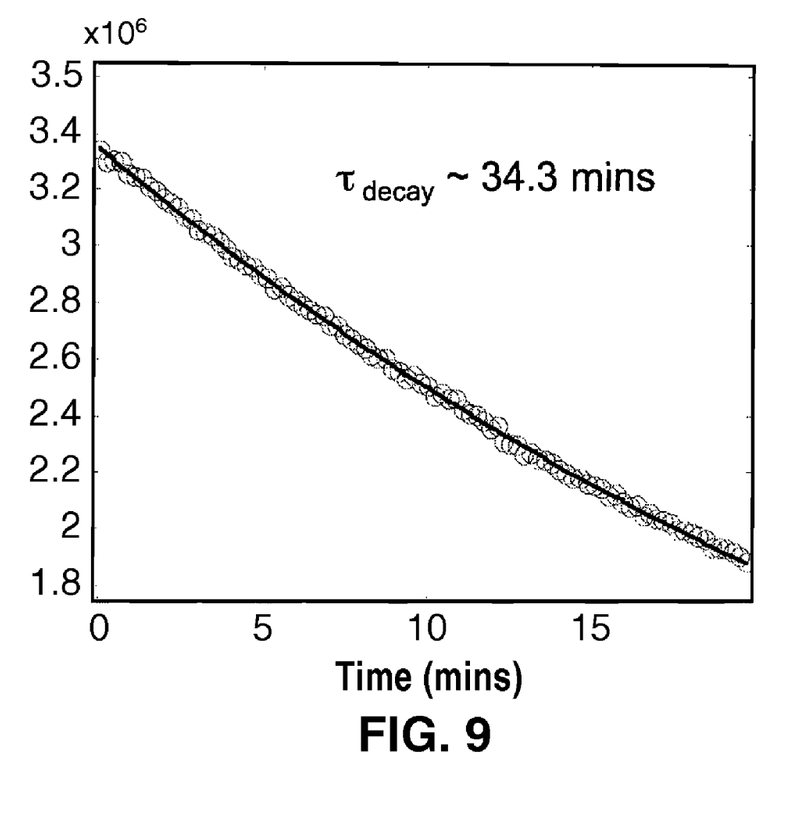
FIG. 9 is a graph of decrease in injected Bg-only fluorescence as a function of time.

For the Bg tagging part of the test, a suspension containing $10^8$ Bg spores per mL of water is injected into the chamber for 12 minutes. A typical particle size distribution histogram of the aerosolized Bg spores is shown in FIG. 6. The injection time was established so that the chamber would contain about $10^8$ Bg spores/m$^3$ at the start of the dye injection. The picogreen dye is then aerosolized into the chamber as before. The temporal evolution of the fluorescence signals observed in the chamber is shown in FIG. 7, which displays the total number of CCD counts found within the laser beam image in a given camera frame. Injection of a Bg/water suspension into the chamber results in a slowly rising concentration of Bg with a characteristic time constant on the order of about 18 minutes, FIG. 8. At the end of the Bg injection period, a few minutes are taken for sample withdrawals to verify Bg concentrations. During this pause, the signal from the Bg-only aerosol exhibits an exponential decay with a time constant of about 34 minutes, FIG. 9. After the pause, the dye is injected, and the signal rapidly rises.

The photon signal is composed of four main sources: ambient room air in the chamber, Bg in a water aerosol, free picogreen dye in a DMSO/water aerosol, and picogreen dye bound to Bg spores. The total observed photon signal is assumed to be due to the linear supposition of these four terms.

Total Signal=Room Air+Bg+Free Dye+Bound Dye

The bound dye signal is obtained by subtracting the room air, Bg and free dye signals from the total.

Bound Dye=Total Signal−Room Air−Bg−Free Dye  (1)

If the contribution from Bg autofluorescence is considered to be part of the detectable signal, then:

Bg+Bound Dye=Total Signal−Room Air−Free Dye  (2)

The free dye signal is obtained independently in the first part of the test procedure. The room air signal is measured just prior to Bg injection. The following bound dye estimates take into account the Bg concentration decay with time by applying an exponential decay correction factor.

For each test, the time evolution of the signals given by (1) and (2) are calculated. A test outcome is considered positive if these values are larger than 3 times the standard deviation of the room air signal at the one minute picogreen injection mark. For a normal distribution, the 99% confidence limit corresponds to 3 standard deviations above the mean, which translates into about a 1% false positive rate.

Figure 10A:
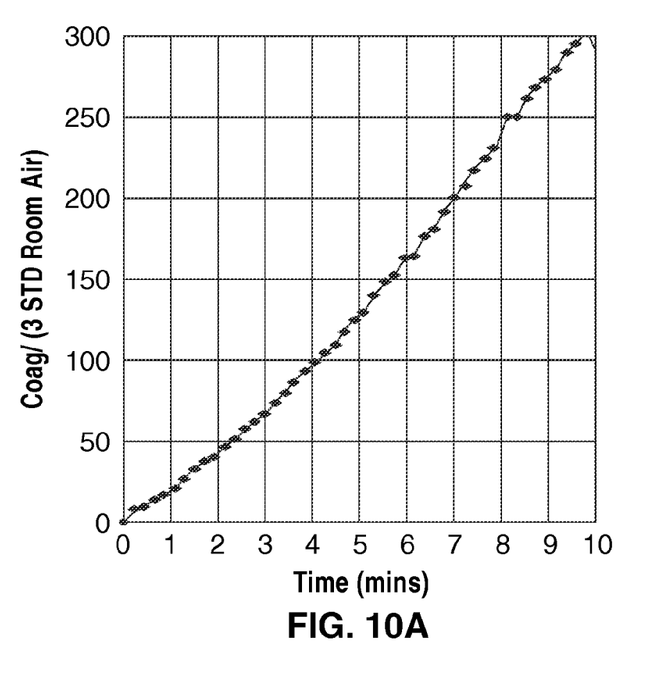
FIGS. 10A-B are graphs of the time evolution of the bound dye and Bg+ bound dye signals, respectively, divided by 3 times the standard deviation of the room air signal.
Figure 10B:
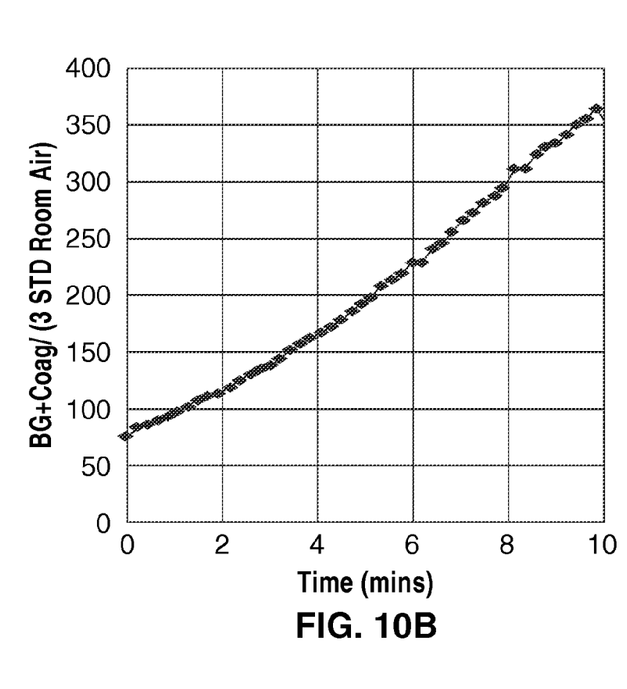
Figure 11A:
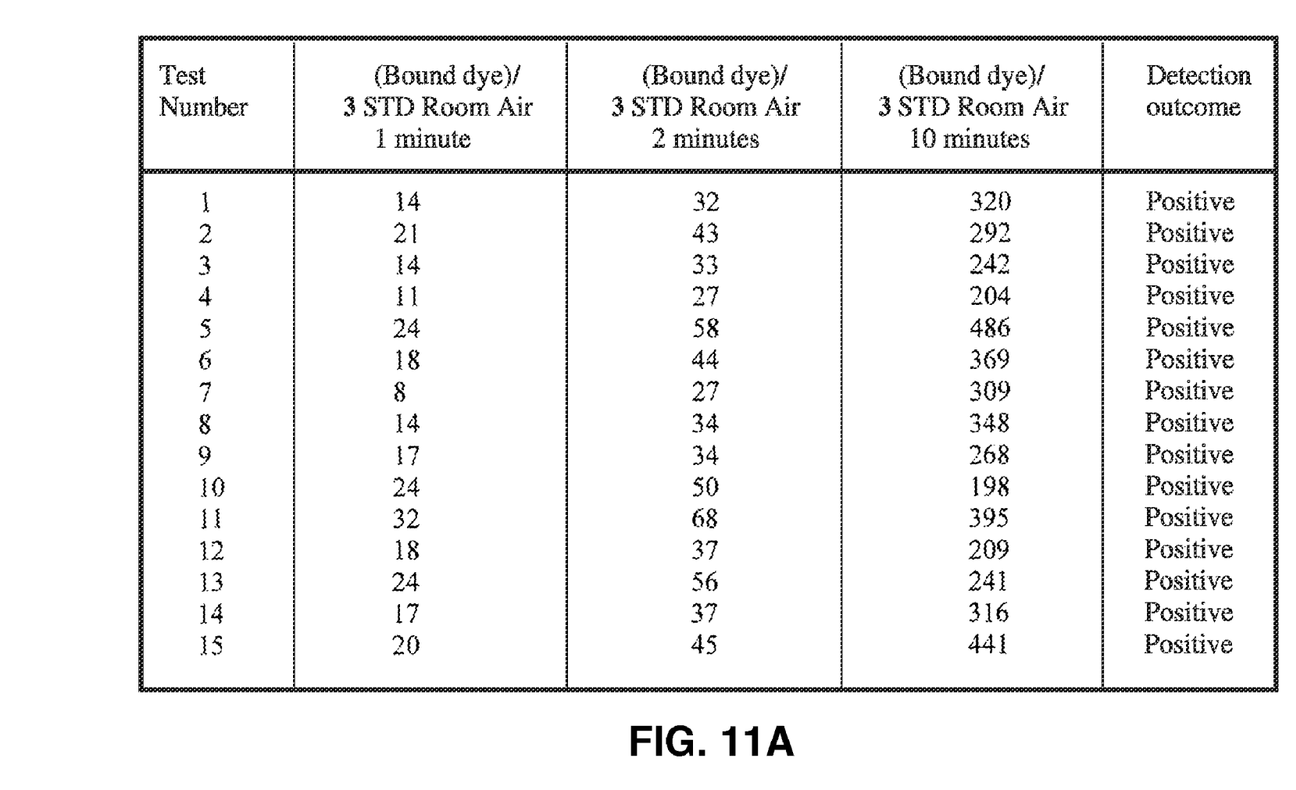
FIGS. 11A-B are tables (Tables 1-2) of results for 15 tests for bound dye and Bg+ bound dye signals, respectively.
Figure 11B:
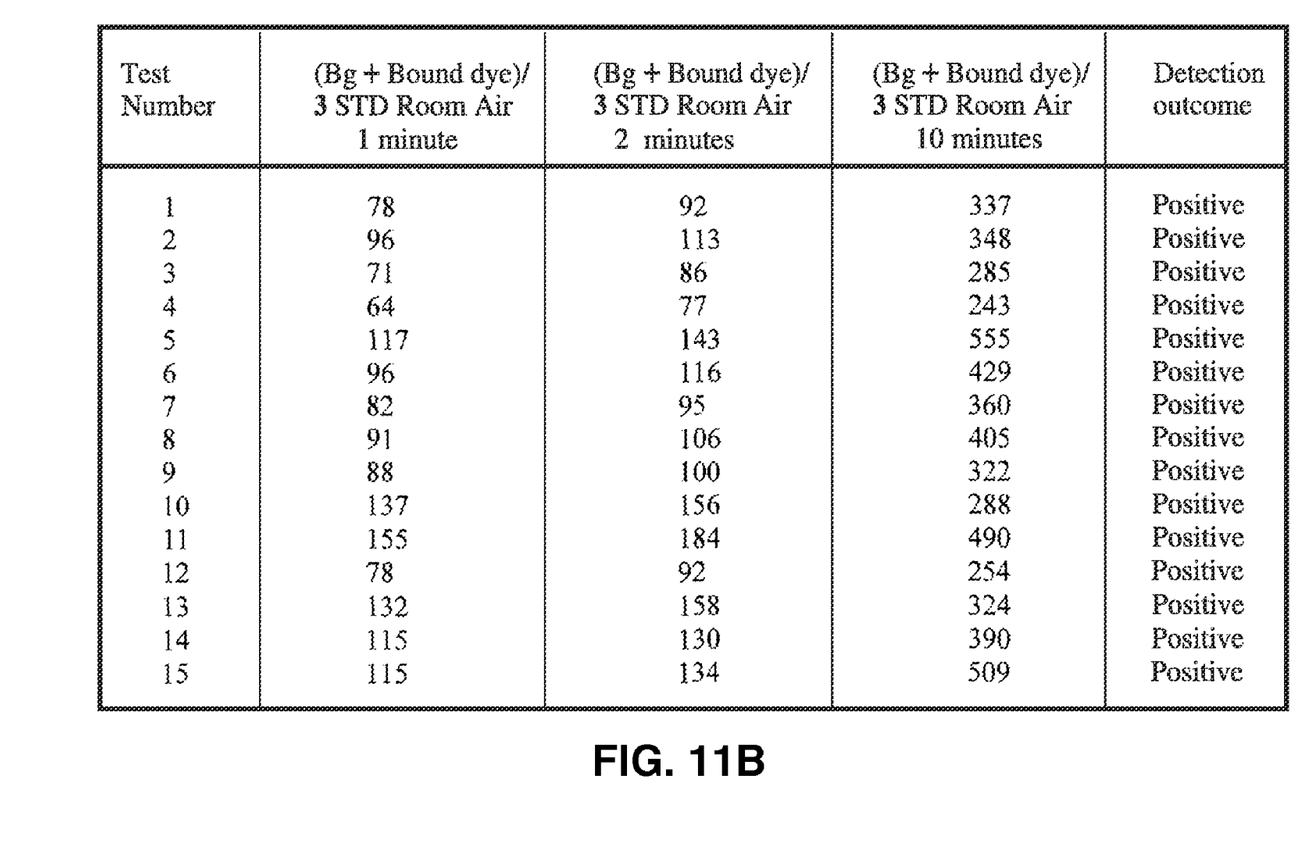

A typical example of the time evolution of the bound dye signal divided by 3 times the standard deviation of the room air signal is shown in FIG. 1A. A typical example of the time evolution of the Bg+ bound dye signal divided by 3 times the standard deviation of the room air signal is shown in FIG. 10B. Results for 15 tests for bound dye and Bg+ bound dye signals respectively are shown in FIGS. 11A-B (Tables 1-2).

A comparison of the 10 minute and 1 minute coagulation (bound dye) signals indicates that at the 1 minute mark the test chamber has not reached the maximum possible coagulation. This is primarily a test chamber dye injector limitation and not a fundamental limit.

The test demonstrate the detection of aerosolized Bg spores in under 1 minute at a concentration of $10^8$/m$^3$ in about a 1 m$^3$ chamber, with a probability of detection of 100% (15 positive tests out of 15). The false positive rate was found to be less than 1%. Based on the obtained mean signal-to-noise (SNR) ratio of 300, the detection limit is estimated to be $10^6$ Bg spores/m$^3$ at a SNR of 3.

The illustrative preferred embodiment described above is directed to the detection of biological particulates using intercalator dyes. Intercalator dyes are specific to the generic class of biological materials since they bind to nucleic acids. Thus if one obtains a positive signal using an intercalator dye, one knows that a biological material is present which can set into motion an appropriate response. Thus the invention is a discriminator between biological and other types of particles, for which a different response may be appropriate. The invention can be implemented to detect chemical or radiological agents by substituting an appropriate taggant that luminesces strongly when bound to chemical or radiological particles. The taggants may be specific to a class of materials or specific to individual species. Taggants may include quantum dots and scintillators. In particular, scintillators may be used to detect radiological particulates. If a scintillator is aggregated onto a target particle, then it would emit light (scintillate) if the target particle is radiological.

The invention thus provides a method and apparatus for real-time detection and discrimination of airborne particulates in the air. This can be implemented as a field system to be deployed for military or other applications. It can also be implemented as an instrument to be used in indoor or outdoor settings to detect a contaminant of interest.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

What is claimed is:

1. A method for detecting airborne target particulates, comprising:
    injecting an aerosol of ultrafine taggant particulates into a region possibly containing the airborne target particulates so that the taggant particulates will bind with the target particulates if they are present;
    directing a light beam at the region into which the taggant aerosol was injected to excite taggant bound to target particulates; and
    detecting luminescence signals from the region, the luminescence signals being characteristic of the taggant binding to target particulates;
    wherein the ultrafine taggant particulates are about a half micron or less in size.

2. The method of claim 1, wherein the taggant particulates have sizes in the range of about 25 nm to about 210 nm.

3. A method for detecting airborne biological particulates, comprising:
    injecting an aerosol of ultrafine taggant particulates into a region possibly containing the airborne biological particulates so that the taggant particulates will bind or coagulate with the biological particulates if they are present, the taggant being specific to nucleic acids and exhibiting a large enhancement of fluorescence upon binding to the biological particulates;

directing a light beam at the region into which the taggant aerosol was injected to excite taggant bound to target particulates; and detecting fluorescence signals from the region, the fluorescence signals being characteristic of the taggant binding to biological particulates;

wherein the taggant particulates have sizes in the range of about 25 nm to about 210 nm.

4. A method for detecting airborne biological particulates, comprising:

injecting an aerosol of ultrafine taggant particulates into a region possibly containing the airborne biological particulates so that the taggant particulates will bind or coagulate with the biological particulates if they are present, the taggant being specific to nucleic acids and exhibiting a large enhancement of fluorescence upon binding to the biological particulates;

directing a light beam at the region into which the taggant aerosol was injected to excite taggant bound to target particulates; and detecting fluorescence signals from the region, the fluorescence signals being characteristic of the taggant binding to biological particulates;

wherein the taggant is an intercalator dye; and wherein the dye is picogreen, the light beam is a 488 nm argon laser beam, and the detected fluorescence signals are in the 525 to 565 nm band.

5. An apparatus for detecting airborne target particulates, comprising:

a taggant aerosol source for injecting an aerosol of ultrafine taggant particulates into a region possibly containing the airborne target particulates so that the taggant particulates will bind or coagulate with the target particulates if they are present;

a light source positioned to direct a light beam at the region into which the taggant aerosol was injected to excite taggant bound to target particles; and a detector positioned to receive luminescence signals from the region, the luminescence signals being characteristic of the taggant binding to target particulates;

wherein the taggant aerosol source contains taggant particulates having sizes in the range of about 25 nm to about 210 nm.

6. The apparatus of claim 5, wherein the target particulates are biological and the taggant aerosol source contains a taggant that is an intercalator dye.

* * * * *